United States Patent [19]

Greville et al.

[11] Patent Number: 5,282,428
[45] Date of Patent: Feb. 1, 1994

[54] MEDICAL NEEDLE INCINERATOR AND SEALER

[75] Inventors: Peter Greville; Mark S. Shurey; Anthony H. Lawrence, all of Limassol, Cyprus

[73] Assignee: Advanced Disposal Systems International Limited, Limassol, Cyprus

[21] Appl. No.: 874,296

[22] Filed: Apr. 24, 1992

[51] Int. Cl.⁵ ............................................. F23G 5/00
[52] U.S. Cl. .................... 110/250; 83/944; 110/346; 128/919; 219/68; 241/65
[58] Field of Search ............ 110/250, 346, 235; 128/919; 219/68; 241/65; 83/944

[56] References Cited

U.S. PATENT DOCUMENTS

| | | |
|---|---|---|
| 2,568,911 | 9/1951 | Cox et al. |
| 4,255,996 | 3/1981 | Choksi et al. |
| 4,445,644 | 5/1984 | Lemke |
| 4,628,169 | 12/1986 | Ching-Lung |
| 4,860,958 | 8/1989 | Yerman |
| 4,877,934 | 10/1989 | Spinello |
| 4,905,916 | 3/1990 | Sorwick et al. |
| 4,934,283 | 6/1990 | Kydd |
| 4,961,541 | 10/1990 | Hashimoto |
| 4,965,379 | 11/1990 | Taylor et al. |
| 4,965,426 | 10/1990 | Colombo |
| 5,005,496 | 4/1991 | Nagata |
| 5,075,529 | 12/1991 | Kudo |
| 5,076,178 | 12/1991 | Kohl et al. ............ 110/250 |
| 5,091,621 | 2/1992 | Butler |
| 5,138,124 | 8/1992 | Kirk et al. |
| 5,138,125 | 8/1992 | Salesses |

FOREIGN PATENT DOCUMENTS

| | | |
|---|---|---|
| 0455075A1 | 6/1991 | European Pat. Off. |
| 9201149 | 1/1993 | PCT Int'l Appl. |
| 89/8607 | 6/1990 | South Africa |

Primary Examiner—Edward G. Favors
Attorney, Agent, or Firm—Dickstein, Shapiro & Morin

[57] ABSTRACT

An incinerator for disposing of a syringe needle having a first pair of electrical contacts adapted to connect a source of electricity at approximately opposed positions across the width of the syringe needle such that the electricity will flow across the width between the positions for welding and sealing the needle, and a second pair of electrical contacts adapted to connect a source of electricity to flow across a portion of the length of the syringe needle for incineration of said portion. The present invention ensures that the end of the needle is completely sealed, i.e., sufficiently sealed to prevent any possible leakage of harmful quantities of fluid.

40 Claims, 8 Drawing Sheets

MEDICAL NEEDLE INCINERATOR AND SEALER

BACKGROUND OF THE INVENTION

The present invention relates to an incinerator, and in particular to an incinerator for incineration (thermal degradation) of electrically conductive hollow articles such as medical needles.

Incinerators particularly adapted for the incineration (thermal degradation) of potentially hazardous used medical needles are disclosed in, for example U.S. Pat. No. 4,628,169 and South African Patent Specification 89/8607. Both documents disclose incinerators for thermally degrading spent syringe needles using a pair of spaced electrical contacts to pass a high current through an interposed medical needle.

We have now devised an improved incinerator which may be used for such purposes.

SUMMARY OF THE INVENTION

To achieve the objects in accordance with the purpose of the invention as embodied and broadly disclosed herein, the present invention provides for an incinerator for disposing of a syringe needle. The incinerator has a first pair of electrical contacts adapted to connect a source of electricity at approximately opposed positions across the width of the syringe needle such that the electricity will flow across the width between the positions for welding and sealing the needle, and a second pair of electrical contacts adapted to connect a source of electricity to flow across a portion of the length of the syringe needle for incineration of said portion.

Advantageously the invention comprises first electrical contact means which are movable relative to one another between a position in which the article is welded and sealed or, in one embodiment, crimped therebetween, and another position in which the first electrical contact means are spaced from the article. Typically the hollow article is welded to provide a substantially sealed termination or end to the hollow article.

It is preferred that the incinerator according to the first aspect of the invention is further provided with a second electrical contact means, these being electrically conductive and spaced from one another defining a gap. The second pair of contacts are typically coupled to power supply means such that an electrical potential difference may exist across the gap between the second pair of contacts. The second pair of contacts are arranged such that when the hollow article is introduced into the incinerator, and where the article comprises an electrically conductive material, the gap between the second pair of contacts is bridged and a current flows through the portion of the article bridging the second pair of contacts. Where the current flowing through the bridging portion of the article is sufficiently high, this portion of the article will be thermally degraded (incinerated) e.g. by melting and thermal oxidation.

In one embodiment, the first electrical contact means are arranged to plastically deform a portion of the article immediately adjacent an incinerated portion.

Typically, the first electrical contact means will also comprise a pair of electrically conductive contacts (sealing contacts) and be arranged for electrical connection to power supply means which may be the same as, or different to, the first mentioned power supply means. An electrical potential difference can therefore exist between the sealing contacts, and when the hollow (conductive) article is sealed, a current flows through the sealed of the article causing the it to be welded, thereby ensuring a good seal is formed.

Advantageously, where the hollow article is elongate (e.g. a medical needle) the first electrical contact means will be spaced from the second electrical contact means in the longitudinal direction of the article.

Typically, in the case where the first electrical contact means are electrically conductive and spaced from the second electrical contact means, a current is caused to flow through the portion of the hollow conductive article between the first and second electrical contact means causing that portion of the hollow article to be incinerated (or pyrolysed).

It is preferred that the first electrical contact means is actuated automatically at a predetermined stage in the incineration process, advantageously being triggered when a predetermined length of the article has been inserted into the incinerator. Typically, insertion of the article into the incinerator causes a movable plunger to complete a circuit when a predetermined plunger position is reached. Completion of this circuit typically causes an electric motor or the like to actuate the first electrical contact means. The plunger may for example contact the actuation arm of a microswitch which actuates a driving motor/leadscrew arrangement to cause a movable sealing contact to move relative to a stationary sealing thereby sealing and welding the article.

It is preferred that the timing and duration of operation of the first electrical contact means and electrical energisation of the second electrical contact means and sealing contacts is controlled by means of appropriate microprocessor and/or integrated circuitry.

The incinerator is preferably provided with a removable receptacle arranged to collect the incinerated (melted) portions of the article.

Typically, the first electrical contact means, and also preferably the second electrical means are provided in a discrete module separable from the remainder of the incinerator. Where the power supply means is provided in the remainder of the incinerator, the discrete module is advantageously provided with electrical coupling means adapted to cooperatively engage with complementary couplings of the power supply means.

The invention will now be further described in a specific embodiment by way of example only and with reference to the accompanying drawings.

DETAILED DESCRIPTION OF THE PREFERRED EMBODIMENT

Figure 1:
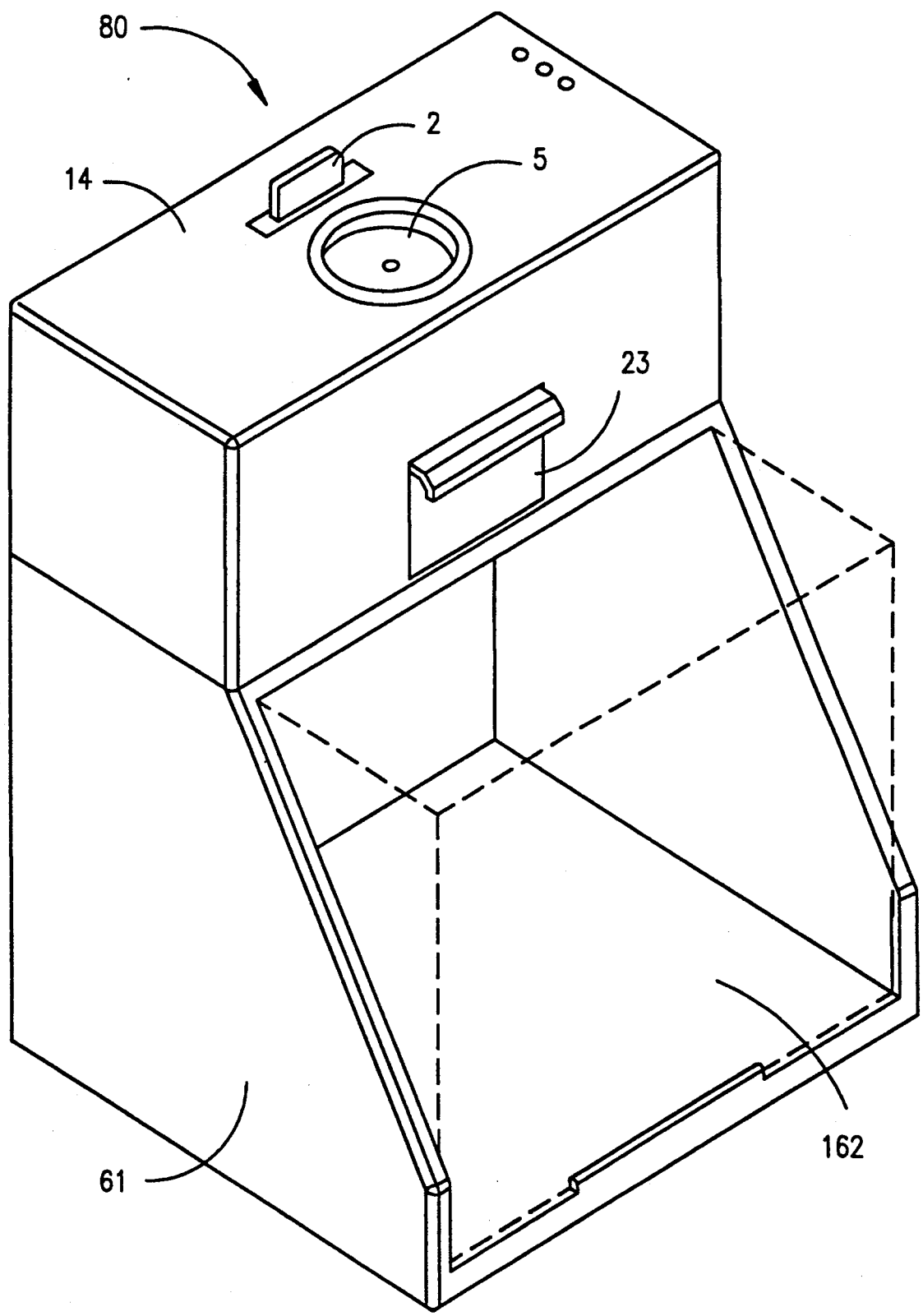
FIG. 1 is an external schematic view of an incinerator according to the invention mounted on a stand.
Figure 2:
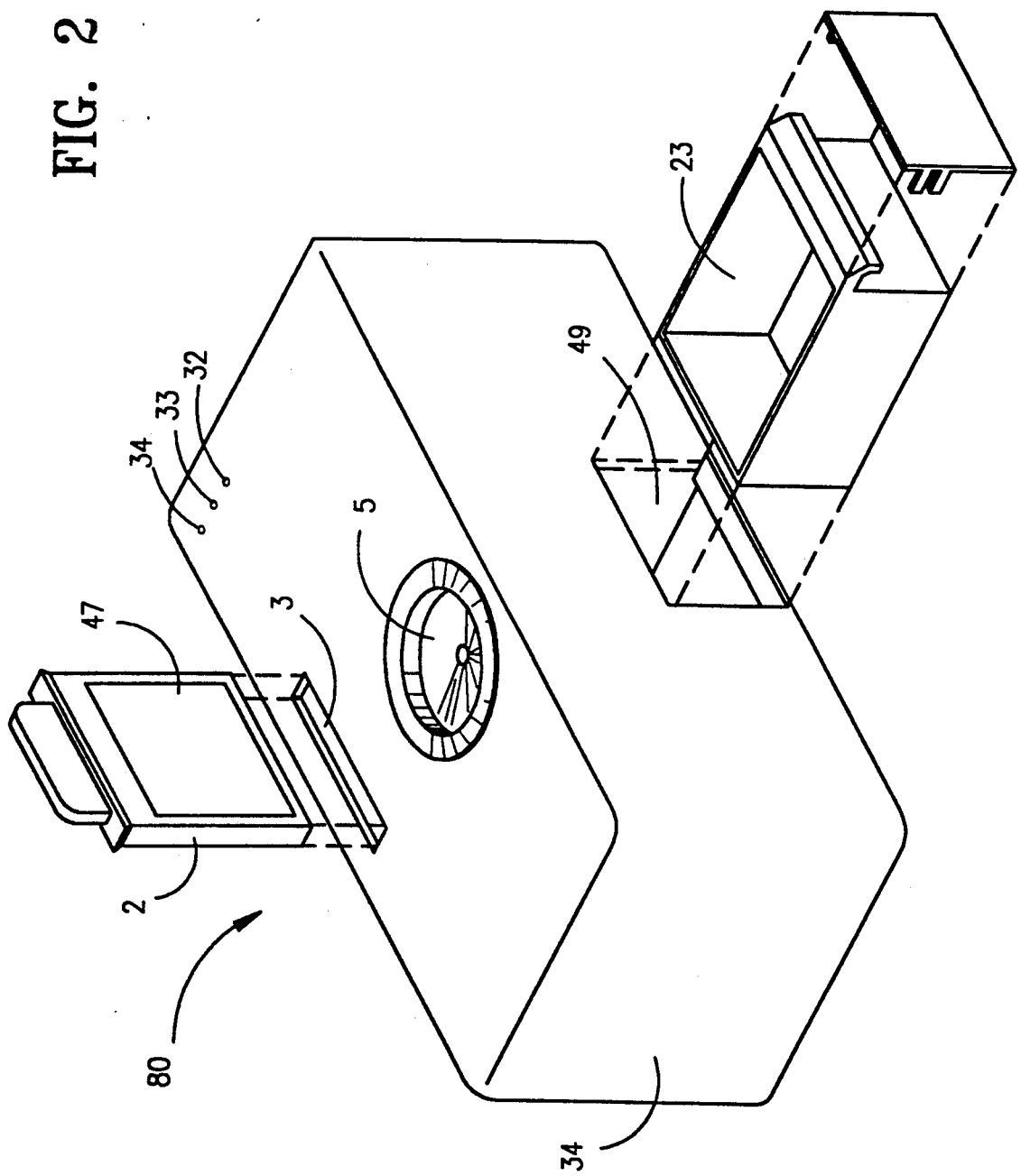
FIG. 2 is an exploded perspective view of the incinerator of FIG. 1.

The incinerator unit, generally designated 80, is typically mounted on a stand 61 which is adapted also to house a general medical waste container 162. The incinerator is particularly adapted for the hygienic destruction of used syringe needles 64 and, since it is portable, the incinerator may conveniently be moved between locations (e.g. in a hospital) where needed.

Referring to FIGS. 1 to 4 in particular, the incinerator comprises a housing 14 provided with a plunger 5 having a central aperture through which the needle to be incinerated is inserted. The plunger 5 moves downwardly relative to the remainder of the housing to trigger the needle incineration cycle as will be explained in more detail below. The housing 14 is provided with a tray receptacle 23 which fits into aperture 49 to collect the incinerated needle (in the form of ash) subsequent to the incineration cycle being completed.

Alternatively, where the waste container 162 is used tray 23 may be removed and the incinerated ash may fall directly into container 162.

The power means for the incinerator is provided either by a main connectable electrical voltage step-down transformer 13 having a primary side 13.1 of 110 V or 220 V/2.5 A and a secondary side 13.2 of 2.5 V/120 A, or rechargeable batteries (not shown).

Status lights 32,33,34 provided on the exterior of the housing enable an operative to ascertain when the incinerator is ready to receive a needle, when the incineration cycle is in operation, and when the rechargeable batteries are in need of recharging.

The incinerator is provided with a fume filtration system comprising an electrically powered fan 4 arranged to draw air (and fumes/dust) from the incineration zone through a filter board 2 to the atmosphere. The filter board 2 includes a filtration sheet 47 adapted to separate the fumes/dust particles from the air exiting to the atmosphere.

Figure 3:
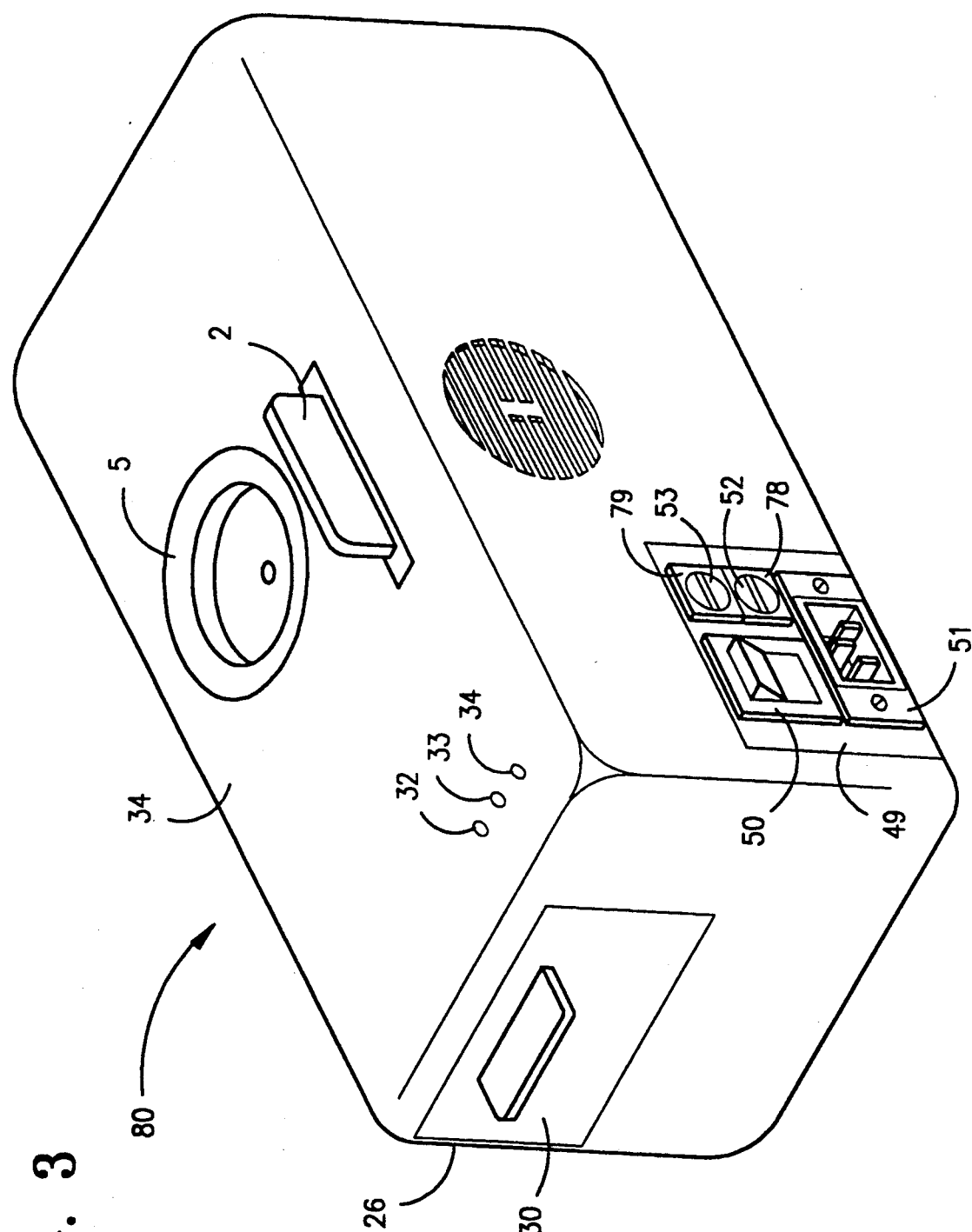
FIG. 3 is a further perspective view of the incinerator of FIGS. 1 and 2.
Figure 4:
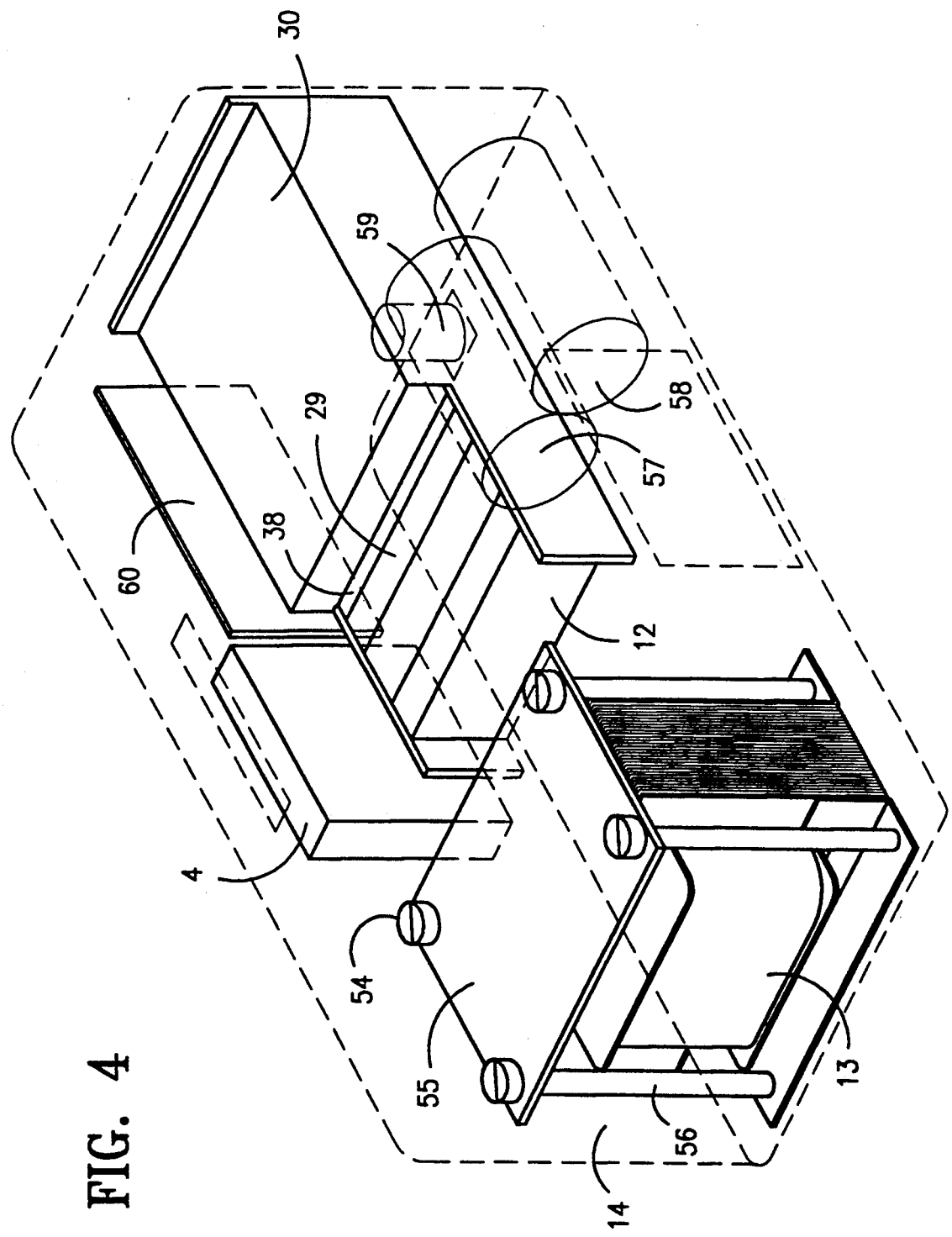
FIG. 4 is a schematic view of the internal structure of the incinerator of FIGS. 1 to 3.
Figure 5:
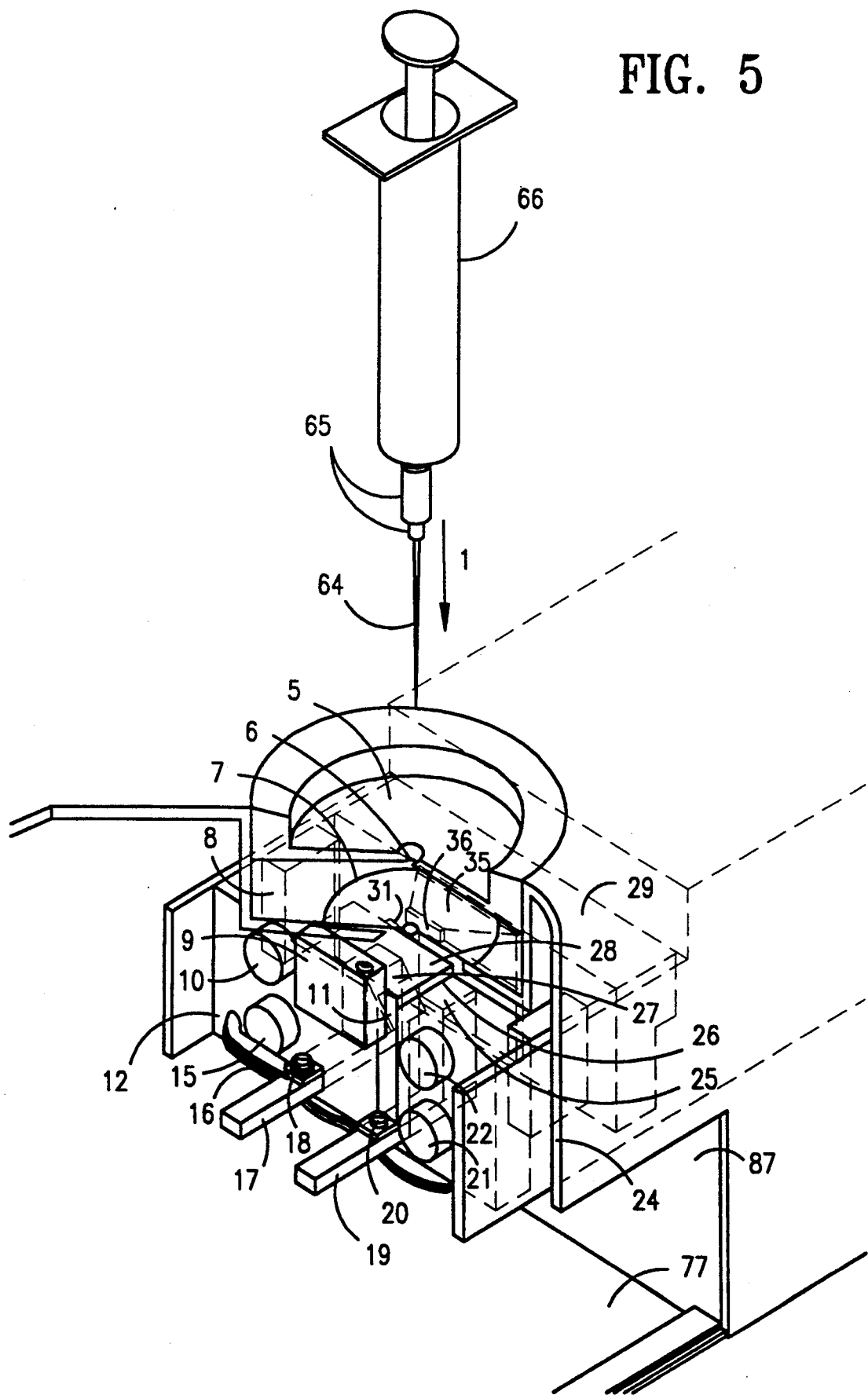
FIG. 5 is a detailed cut-away view of a part of the incinerator of FIGS. 1 to 4.
Figure 6C:
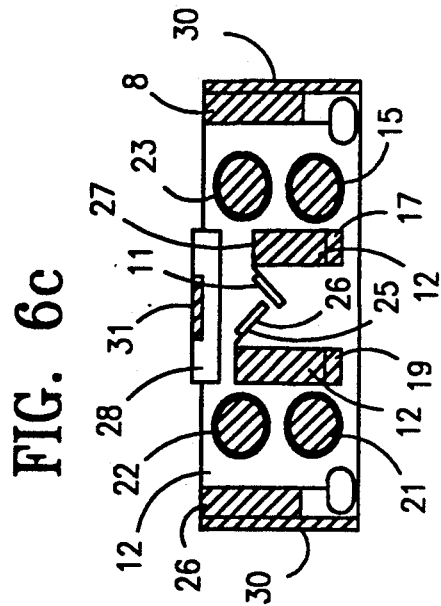
FIGS. 6a to 6d are schematic and sectional views of a part of the incinerator of FIGS. 1 to 5.
Figure 6D:
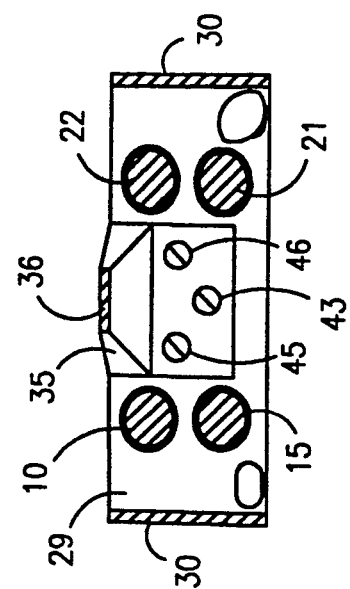
Figure 6A:
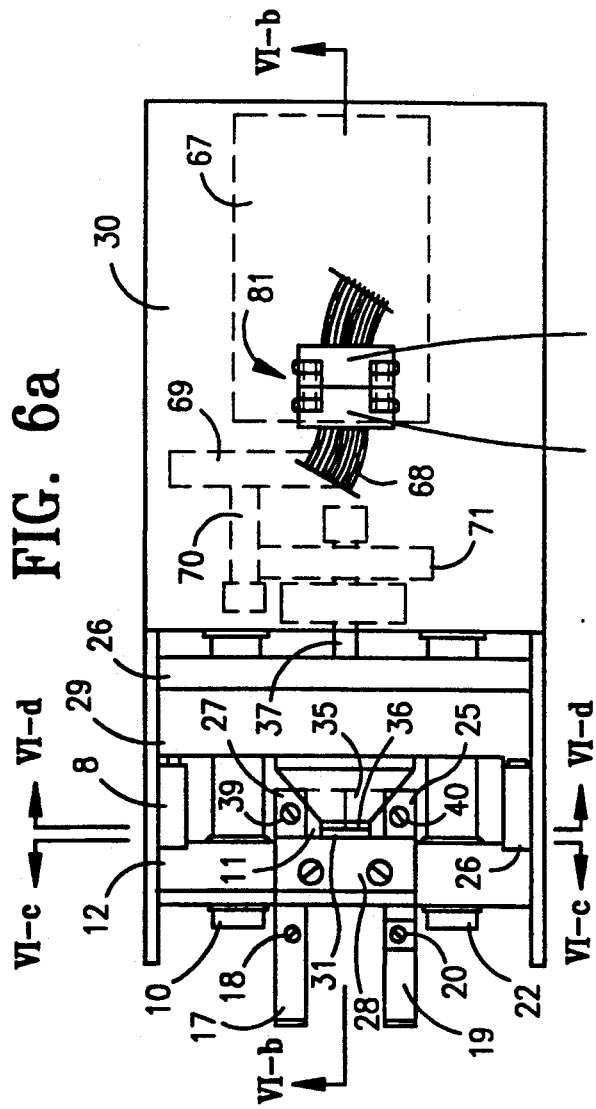
Figure 6B:
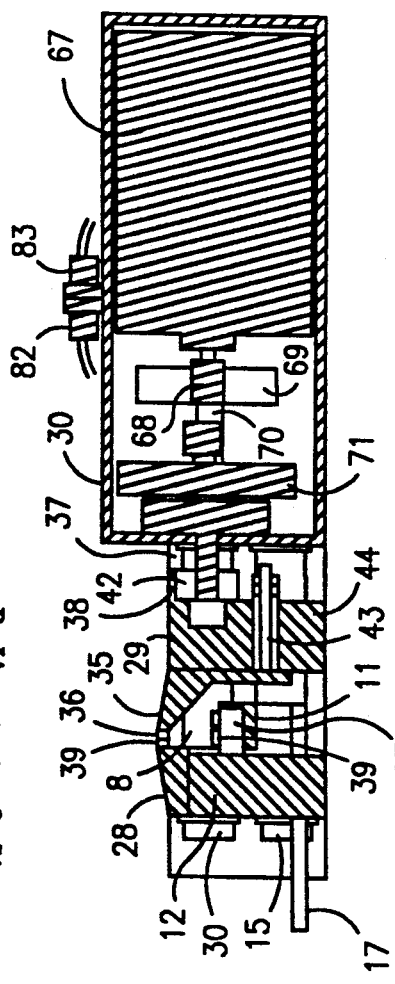
Figure 7A:
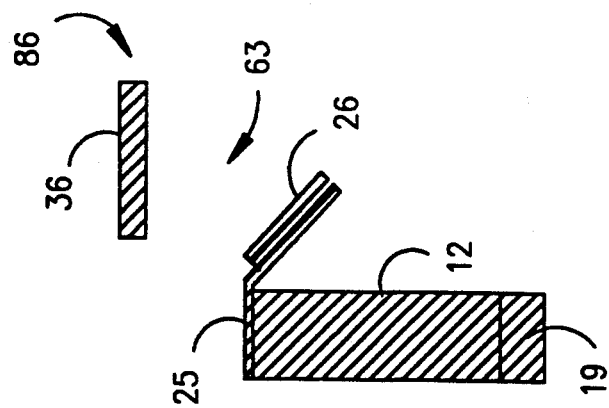
FIGS. 7a to 7c are schematic sectional views of parts of the incinerator shown in FIGS. 5 to 6d.
Figure 7B:
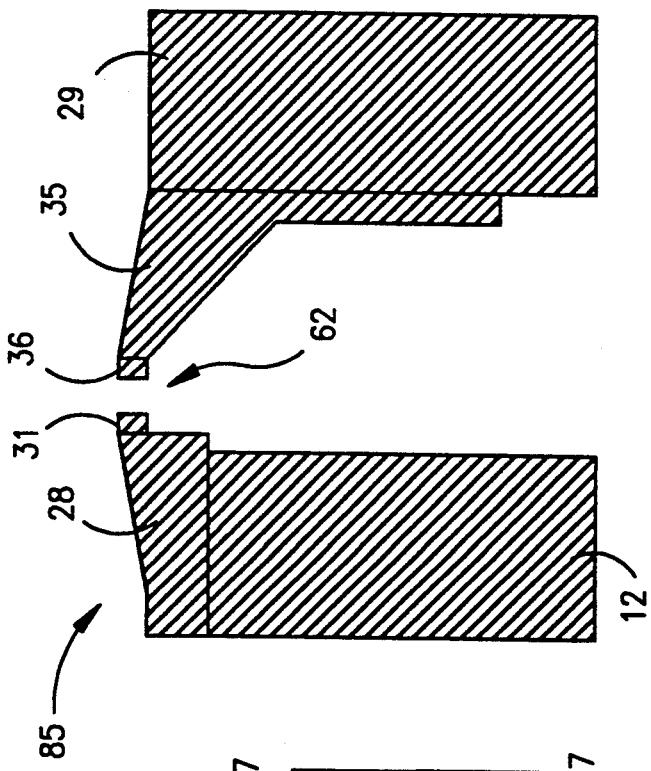
Figure 7C:
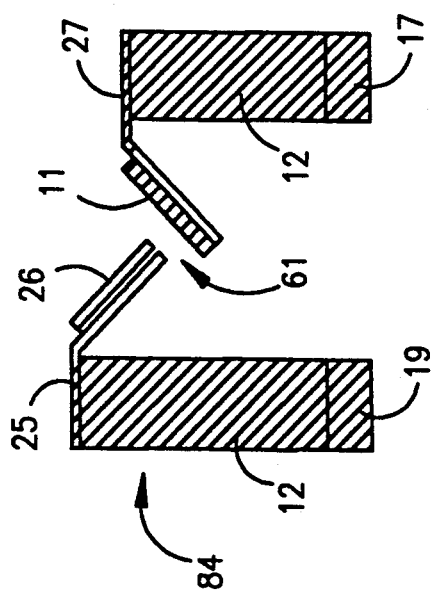
Figure 8:
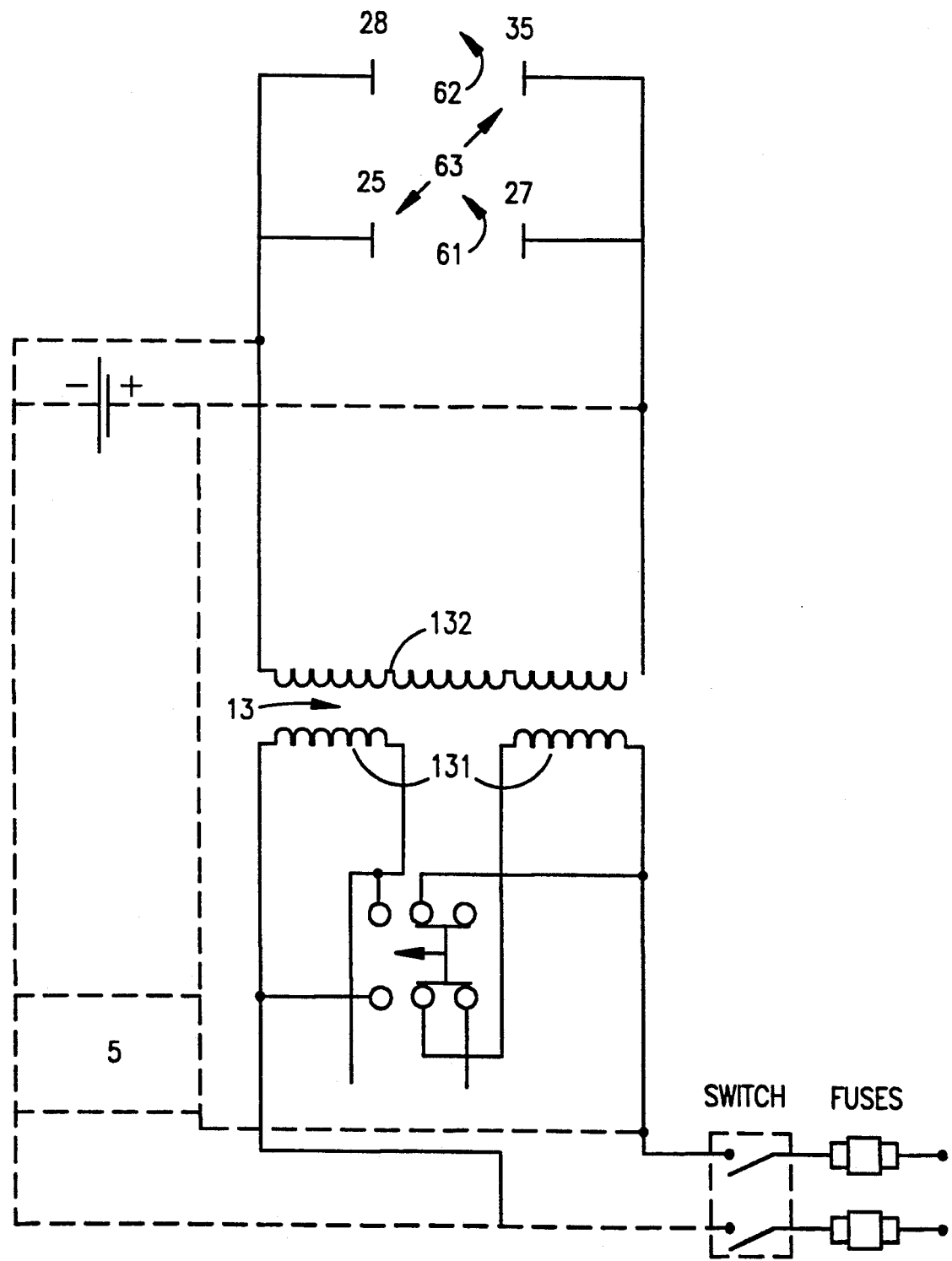
FIG. 8 is a schematic view of the operational electrical circuitry of the incinerator of FIGS. 1 to 7c.

Referring to FIG. 3, the control/interface panel on the rear of the housing can clearly be seen showing the main plug socket 51, on/off switch 50 and fuses 52,53 and fuse holders 78,79. Also shown in FIG. 3 is the incineration module 30 which is removable from the remainder of the incinerator housing, and described in greater detail below.

Referring now to FIGS. 4 to 7c in particular, the incineration module 30 slides into the housing 14 (on guide rods 10,15,21,22) and electrical contact is made with the power supply means by conductive contact pins 17,19, thereby setting up an electrical potential difference between incineration electrodes 25/26 and 27/11. The structural configuration of the incineration module may be best described with reference to its use below.

A needle 64 of a medical syringe 66 is inserted through the central aperture in the plunger 5. As the needle 64 is pushed downwardly, it is guided into a hole in washer 7 until the longitudinal side of the needle touches the incineration electrode 25/26 and the tip of the needle touches the incineration electrode 27/11. At this stage the contact means 84 (see FIG. 7a) is completed between electrodes 25/26 and 27/11 across gap 61. Since the current supplied between the electrodes is sufficiently high (approximately 120A—see above) the temperature of the needle between the contact electrodes is raised to between 800° and 1000° C. and incineration (or disintegration) of the needle between electrodes 25/26 and 27/11 is effected. This process continues as the needle is pushed down until eventually the needle hub 65 contacts the plunger 5. Since the needle hub 65 is of greater diameter than the aperture in plunger 5, continued downward pressure on syringe 66 causes the plunger 5 to travel down the complementary recess 6 causing the needle to continue its downward passage and incineration of the portions of the needle contacting and intermediate incineration electrodes 25/26 and 27/11 to continue as described above.

Eventually, the base of the plunger contacts the lever arm of a microswitch 9. Microswitch 9 is connected to a relay switch which completes a circuit to a motor 67 housed in the incineration module 30. Motor 67 drives a lead screw 37 which urges a movable section of module 30 towards a stationary section 12,28,31 of the module. The movable section comprises components 29,35,36. As the movable section nears the stationary section, the portion of the needle 64 immediately adjacent the hub 65 (which has not at this point bridged gap 61 and has therefore not been incinerated) is sealed between sealing contacts 31,36 (see FIG. 7b) on the stationary and movable sections of housing 30 respectively. Since the sealing contacts 31,36 are connected to the power supply (and therefore an electrical potential difference exists between them across gap 62—see FIG. 7b) once the needle is sealed between the contacts and the circuit between them across gap 62 is completed, the sealed end of the needle is incinerated, effectively ensuring sending of the (now reduced) end of the needle and preventing possibly contaminating fluids escaping from the syringe 66. Whilst the needle is being sealed between the sealed contacts 31,36, a third circuit is completed between contacts 25/26 and 36 across gap 63. The portion of the needle extending across the gap 63 (i.e. below the sealed portion of the needle) is therefore also incinerated (see FIG. 7c). The microswitch 9 is set to trip the relay when the gap 62 between contact electrodes 31 and 36 is approximately 0.5 mm. At this point the polarity of the motor 67 is reversed causing the movable section (29,35,36) of incineration module 30 to separate from the stationary section. The separation is continued until microswitch 24 is actuated causing the motor to stop and the contacts to reset themselves ready for the next needle to be incinerated. The operation of the timing circuitry and motor/power switching is controlled by microprocessors provided on printed circuit boards 60 contained within the incinerator housing 14. Once a needle has been incinerated and sealed and in one embodiment also crimped (i.e. once the incineration/sealing cycle is complete) the sealed needle 64 (still connected to syringe 66) is removed from the aperture in plunger 5, and the plunger 5 is reset to its starting position under the influence of four biasing springs (not shown).

The syringe 66 which now has only a very short portion of crimped in one embodiment and sealed needle 64 projecting therefrom may then be sent for disposal with the risk of potentially hazardous fluids escaping from the syringe and needlestick injury substantially reduced. The incinerated material from the needle (comprising of an ash or powder like material) is deposited in the waste tray 23 or a general medical waste container 162 under gravity.

Typically, the electrode (incineration) contacts 26,11,31,36 comprise 90% silver: 10% cadmium which has been found effective in inhibiting fusing (or welding) of the needle 64 to the contacts during incineration. A particularly advantageous feature of the incinerator according to the invention is the facility to completely remove the incinerator module 30 from the remainder of the incinerator for periodic overhaul or cleaning.

What is claimed as new and desired to be protected by Letters Patent of the United States is:

1. An incinerator for disposing of a syringe needle comprising:

first electrical contact means for connecting a source of electricity at approximately opposed positions across the width of the syringe needle for the electricity to flow across the width between the opposed positions for welding and sealing the needle; and second electrical contact means for connecting a source of electricity to flow across a portion of the length of the syringe needle for incineration of said portion.

2. An incinerator as in claim 1 wherein said first electrical contact means includes a first sealing contact and a second sealing contact positioned to contact the side of the needle at approximate opposed positions across the width of the needle, said first and second sealing contacts being separated by a first gap.

3. An incinerator as in claim 2 wherein said second electrical contact means includes a side electrode contact positioned to contact the side of the needle and a tip electrode contact positioned to contact the tip of the needle, said side and tip electrode contacts being separated by a second gap.

4. An incinerator as in claim 3 further comprising electrical power supply means for supplying said source of electricity to said side contact and said tip contact.

5. An incinerator as in claim 4 wherein said supply means delivers enough electricity to raise said needle portion to between about 800 to about 1000 degrees Celsius.

6. An incinerator as in claim 3 wherein said supply means delivers approximately 120 amps of electricity.

7. An incinerator as in claim 6 further comprising moving means for moving at least one of said first and second sealing contacts towards the other to contact the side of the needle to make electrical contact therewith.

8. An incinerator as in claim 7 wherein said electrical supply means further supplies said source of electricity to said sealing contacts at a sufficient current and voltage for the sealing of the needle.

9. An incinerator as in claim 7 wherein said moving means causes said sealing contacts to contact the needle with sufficient force to crimp the needle.

10. An incinerator as in claim 3 further comprising third electrical contact means for connecting a source of electricity across a remaining portion of the length of the syringe needle extending between said sealing contacts and the tip of the needle for incineration of said remaining portion.

11. An incinerator as in claim 10 wherein said third contact means includes said side contact and one of said sealing contacts.

12. An incinerator as in claim 1 wherein said contact means includes electrical contacts composed of about 90 percent silver and about 10 percent cadmium.

13. An incinerator as in claim 8 wherein said supply means includes a rechargeable battery and said incinerator is configured to be portable by a hospital worker.

14. An incinerator for disposing of a syringe needle comprising:

a first pair of electrical contacts adapted to connect a source of electricity at approximately opposed positions across the width of the syringe needle such that the electricity will flow across the width between the positions for welding and sealing the needle; and, a second pair of electrical contacts adapted to connect a source of electricity to flow across a portion of the length of the syringe needle for incineration of said portion.

15. A method for disposing of a hypodermic needle comprising the steps of:

providing first electrical contact means for connecting a source of electricity across the width of the hypodermic needle for sealing the needle, and second electrical contact means for connecting a source of electricity across a portion of the length of the syringe needle for incineration of said portion;

operating said second electrical contact means to incinerate said portion of said needle; and, operating said first electrical contact means to seal the needle.

16. A method as in claim 15, wherein said second electrical contact means is operated before said first electrical contact means.

17. An incinerator as in claim 14 wherein said first pair of electrical contacts includes a first sealing contact and a second sealing contact positioned to contact the side of the needle at approximate opposed positions across the width of the needle, said first and second sealing contacts being separated by a first gap.

18. An incinerator as in claim 17 wherein said second pair of electrical contacts includes a side electrode contact positioned to contact the side of the needle and a tip electrode contact positioned to contact the tip of the needle, said side and tip electrode contacts being separated by a second gap.

19. An incinerator as in claim 18 further comprising an electrical power supply adapted to for supply said source of electricity to said side contact and said tip contact.

20. An incinerator as in claim 19 wherein said supply is adapted to deliver enough electricity to raise said needle portion to between about 800 to about 1000 degrees Celsius.

21. An incinerator as in claim 18 wherein said supply is adapted to deliver approximately 120 amps of electricity.

22. An incinerator as in claim 21 further comprising a motor in driving relationship with at least one of said first and second sealing contacts to move said at least one contact towards the other to contact the side of the needle to make electrical contact therewith.

23. An incinerator as in claim 22 wherein said electrical supply is further adapted to supply said source of electricity to said sealing contacts at a sufficient current and voltage for the sealing of the needle.

24. An incinerator as in claim 23 wherein said motor is adapted to drive said sealing contacts to contact the needle with sufficient force to crimp the needle.

25. An incinerator as in claim 18 further comprising a third pair of electrical contacts adapted to connect a source of electricity across a remaining portion of the length of the syringe needle extending between said sealing contacts and the tip of the needle for incineration of said remaining portion.

26. An incinerator as in claim 25 wherein said third pair of contacts includes said side contact and one of said sealing contacts.

27. An incinerator as in claim 14 wherein at least one of said contacts is made from a material including silver.

28. An incinerator as in claim 27 wherein said at least one of said contacts is made from a material including cadmium.

29. An incinerator as in claim 28 wherein said at least one of said contacts is made from a material including about 90 percent silver and about 10 percent cadmium.

30. An incinerator as in claim 29 wherein the entire portion of the surface of said at least one of said contacts that touches the needle is composed of said material to inhibit the welding of the needle to said contact.

31. An incinerator as in claim 23 wherein said supply means includes at least one rechargeable battery and said incinerator is configured to be portable by a hospital worker.

32. An incinerator as in claim 14 further comprising a housing enclosing said contacts, a filter, and a fan positioned to move fumes from an incinerator zone, through the filter to exit said housing.

33. An incinerator as in claim 23 further comprising a plunger having an aperture through which the needle of the syringe extends, said plunger being mounted for translational movement in the direction of the longitudinal axis of the needle, said plunger being positioned between the needle hub of the syringe and said contacts.

34. An incinerator as in claim 33 wherein said aperture of said plunger is smaller than the needle hub, and the plunger is movable in the direction of said contacts by an operator pushing on the syringe to cause the needle hub to urge against said plunger.

35. An incinerator as in claim 34 wherein said electrical supply includes a motor switch positioned to be activated by the movement of said plunger to a predetermined position, said switch connecting said supply to said motor such that when said motor switch is activated, said motor drives said at least one sealing contact towards the other.

36. An incinerator as in claim 35 further comprising a trip switch connected to reverse said motor after the needle has been welded by said sealing contacts, to move said sealing contacts apart.

37. An incinerator as in claim 22 wherein one of said contacts is mounted to remain stationary and the other is mounted to be driven by said motor towards said stationary contact.

38. A method as in claim 16 further comprising the steps of:
   a. providing a plunger having an aperture through which the needle, but not entire syringe, may extend, and a motor connected to move said first electrical contact means in contact with the needle;
   b. inserting the needle through said aperture to extend across said second electrical contact means;
   c. then operating said second electrical contact means;
   d. repeating steps c. and d. until said plunger is engaged and moved by the syringe to a predetermined position;
   e. operating said motor to move said first electrical contact means in contact with the needle;
   f. then operating said first electrical contact means to weld and seal the end of the needle to prohibit the exit of any fluids through the needle from the syringe.

39. A method as in claim 38 further comprising the steps of: providing third electrical contact means for connecting a source of electricity across a remaining portion of the needle between said first electrical contact means and the tip of the needle for the incineration of the remaining portion; operating said third electrical contact means after the operation of said first electrical contact means to incinerate said remaining portion.

40. The method of claim 39 wherein said motor moves said first electrical contact means in contact with the needle with sufficient force to crimp the needle.

* * * * *